United States Patent
Haviv et al.

(12) 
(10) Patent No.: US 6,297,354 B1
(45) Date of Patent: Oct. 2, 2001

(54) PENTAPEPTIDE LHRH ANTAGONISTS

(75) Inventors: Fortuna Haviv, Deerfield; Wesley Dwight, Evanston; Jonathan Greer, Chicago, all of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/373,180

(22) Filed: Aug. 12, 1999

Related U.S. Application Data

(60) Provisional application No. 60/096,292, filed on Aug. 12, 1998.

(51) Int. Cl.[7] .......................... C07K 16/00; A61K 38/08; A61K 38/09
(52) U.S. Cl. .......................... 530/313; 530/330; 530/333; 530/338; 530/339; 530/344; 530/345; 514/17; 514/908
(58) Field of Search ..................................... 530/313, 330, 530/333, 338, 339, 344, 345; 514/17, 908

(56) References Cited

U.S. PATENT DOCUMENTS

| | | | |
|---|---|---|---|
| 4,043,993 | 8/1977 | Tinney et al. | 260/112.5 |
| 4,043,994 | 8/1977 | Wittle et al. | 260/112.5 |
| 4,062,835 | 12/1977 | Tinney | 260/112.5 |
| 4,405,607 | 9/1983 | Cardinaux et al. | 260/112.5 |
| 5,110,904 | 5/1992 | Haviv et al. | 530/313 |
| 5,140,009 | 8/1992 | Haviv et al. | 530/313 |
| 5,502,035 | 3/1996 | Haviv et al. | 530/313 |
| 6,191,115 | * 2/2001 | Haviv | 530/313 |

FOREIGN PATENT DOCUMENTS

| | | |
|---|---|---|
| A20417454 | 3/1991 | (EP) . |
| A30417454 | 3/1991 | (EP) . |

OTHER PUBLICATIONS

Janecka, et al., "Reduced–Size Antagonists of Lutenizing Hormone–Releasing Hormone Active in vitro" *Journal of Medicinal Chemistry*, vol. 38 (1995), pp. 2922–2924.

Janecka, et al., "The Structural Features of Effective Antagonists of the Luteinizing Hormone Releasing Hormone", *Amino Acids*, vol. 6 (1994), pp. 111–130.

Chang, et al., "Studies on Analogs of the Luteinizing Releasing Hormone Towards Elucidation of the Release Mechanism", *Biochemical and Biophysical Research Communications*, vol. 47 (1972), pp. 1256–1261.

Schally, et al., "Hypothalamic Follicle–Stimulating Hormone (FSH) and Luteinizing Hormone (LH)–Regulating Hormome: Structure, Physiology, and Clinical Studies", Fertility and Sterility, vol. 22, No.11, (Nov.1971), pp. 703–721.

Schally, "Aspects of Hypothalamic Regulation of the Pituitary Gland", Science, vol. 202 (Oct. 6, 1978), pp. 18–28.

* cited by examiner

*Primary Examiner*—F. T. Moezie
(74) *Attorney, Agent, or Firm*—Steven F. Weinstock

(57) ABSTRACT

The present invention relates to a class of pentapeptide analogs of LHRH. These compounds are useful in the treatment of disease conditions which are mediated by reproductive hormones, including benign prostate hyperplasia, prostate tumors, breast and ovaries tumors, cryptorchidism, hirsuitism, gastric motility disorders, dysmenorrhea, and endometriosis.

8 Claims, No Drawings

SEQUENCE LISTING

<160> NUMBER OF SEQ ID NOS: 1

<210> SEQ ID NO 1
<211> LENGTH: 10
<212> TYPE: PRT
<213> ORGANISM: Homo sapiens

<400> SEQUENCE: 1

Glu His Trp Ser Tyr Gly Leu Arg Pro Gly
1               5                   10

PENTAPEPTIDE LHRH ANTAGONISTS

This application claims the benefit of the provisional application 60/096,292, filed on Aug. 12, 1998 now abandoned.

TECHNICAL FIELD OF INVENTION

The present invention relates to novel analogs of LHRH. The novel analogs provide pentapeptides truncated from both the N-terminus and the C-terminus of LHRH antagonist peptides. The invention also relates to processes for preparing the disclosed compounds, pharmaceutical compounds containing such compounds, and use of such compounds for modulating levels of sex hormones in male or female mammals.

BACKGROUND OF THE INVENTION

Luteinizing hormone releasing hormone (LHRH) is released from the hypothalamus and binds to a receptor on the pituitary gland causing the release of gonadotropin hormones. The gonadotropin hormones, luteinizing hormone (LH) and follicle-stimulating hormone (FSH), secreted from the anterior pituitary gland, regulate the fundamental reproductive processes, such as ovarian release and gamete maturation. These hormones play a major role in regulating the synthesis of the steroidal reproductive hormones from the gonads, ie. estrogen and progesterone in females and testosterone in males.

The ongoing system of feedback between hypothalamus, the anterior pituitary gland, and the gonads modulates the fundamental processes related to the reproductive cycle. The feedback process, described by A. V. Schally et al., *Fertility and Sterility*, 22:11 (1971), provides a web of complex relationships related to reproductive function. Pulsatile release of the gonadotropin hormones controls levels of steroidal hormone circulating in the mammalian reproductive cycle. Manipulation of the release of these hormones provides an avenue for the design of novel compounds useful in treating various conditions related to dysfunction of the reproductive cycle and hormone dependent diseases. Several agonists of natural LHRH have been shown to be clinically useful.

Natural mammalian releasing hormone LHRH isolated and purified from porcine and human hypothalami has been characterized as having the sequence:

(Pyro)Glu-His-Trp-Ser-Tyr-Gly-Leu-Arg-Pro-Gly-NH$_2$   SEQ ID NO:1 as described in A. V. Schally, *Science*, 202:6 (1978). Substitutions and derivatizations of amino acyl residues have been developed to achieve novel compounds useful in treating various disorders related to mammalian reproductive systems.

Synthetic analogs of LHRH have been described in a number of U.S. patents for exhibiting activity as LHRH agonists or as antagonists of LHRH. For the most part; these compounds contain nine or ten amino acyl residues, substituting naturally-occurring or non-naturally occurring amino acid residues at one or more positions in the natural sequence of LHRH. U.S. Pat. No. 5,110,904 describes nonapeptide and decapeptide LHRH antagonists wherein the nitrogen atom of at least one of the amide bonds has been alkylated. The decapeptide and undecapeptide analogs described in U.S. Pat. No. 5,502,035 have an acyl-substituted N-terminal nitrogen atom.

Truncated peptide compounds have been developed as a series of smaller peptide analogs also exhibiting biological activity and having the added advantage of possibly improved oral bioavailability. These reduced-size peptides, described in U.S. Pat. No. 5,140,009, exhibit effective LHRH agonist or antagonist activity. They are "pseudo" hexapeptide, heptapeptide, octapeptide and nonapeptide analogs of LHRH, which have the 1 to 3 amino acids eliminated from the N-terminus of a decapeptide sequence to achieve activity as LHRH antagonists. Copending U.S. application Ser. No. 09/133,055, now abandoned, and U.S. application Ser. No. 09/232,425, filed Jan. 15, 1999, disclose and describe a class of heptapeptide LHRH analogs wherein the 10 to 8 amino acids are eliminated from the C-terminus of a decapeptide LHRH antagonist.

The development of synthetic LHRH antagonists truncated from the C- and N-termini having biological activity provides novel compounds for treatment of hormone dependent diseases in male and female mammals. Smaller synthetic peptides provide significant advantages when compared to decapeptide LHRH analogs. These LHRH antagonists are useful in the treatment of a variety of conditions in which the suppression of sex steroids plays a major therapeutic role that includes delay of puberty, treatment of benign prostatic hyperplasia, palliative treatment or remission of hormonal-dependent tumors of breast and ovaries, palliative treatment or remission of hormonal-dependent tumors of the prostate, the treatment of cryptorchidism, hirsutism in women, gastric motility disorders, dysmenorrhea and endometriosis.

SUMMARY OF THE INVENTION

Compounds of the invention are peptides have the 1 to 3 amino acids eliminated from the N-terminus and the 10 to 8 amino acids eliminated from the C-terminus. The present invention provides a novel LHRH analog having a formula:

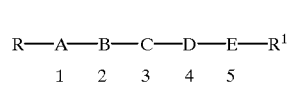

(I)

as defined herein as well as the preferred and representative compounds described. The compounds provide LHRH analogs having a molecular weight suitable for possible improved oral bioavailability for treatment of disorders related to abnormal levels of reproductive hormones. The compounds of the invention relate to LHRH analogs wherein two amino acids from the N-terminus and three amino acids from the C-terminus of a decapeptide sequence has been eliminated to provide a pentapeptide having LHRH antagonist activity.

Another aspect of the invention relates to pharmaceutical formulations comprising the compounds of the invention or pharmaceutically acceptable salts, esters, or prodrugs thereof.

In another aspect, the invention relates to a method of modulating gonadotropin hormones in a mammal comprising administering to a mammal in need of such treatment a therapeutically effective amount of a compound as defined above.

Yet another aspect of the invention relates to a process for preparing compounds of the invention or pharmaceutically acceptable salts, esters, or prodrugs thereof.

DETAILED DESCRIPTION OF THE INVENTION

The invention comprises a compound of the formula:

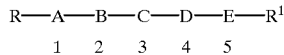
(I)

or a pharmaceutically acceptable salt, ester, or prodrug thereof, wherein:

R is of the formula wherein X is hydrogen, lower alkyl, alkoxy, or a halide selected

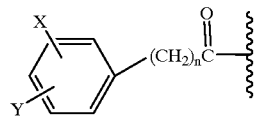

from the group consisting of bromide, chloride, fluoride, and iodide; Y is hydrogen or loweralkyl; and n is 1–3.

A is an amino acid residue selected from 3-(1-naphthyl)-D-alanyl, 3-(1-naphthyl)-L-alanyl, D-tryptyl, D-3-(4,4'-biphenyl)alanyl, D-(benzthienyl)alanyl, and glycyl.

B is seryl or glycyl.

C is an amino acid residue selected from (N-epsilon-nicotinyl)lysyl, N-methylphenylalanyl, (4-N-nitro)-N-methylphenylalanyl, [4-(3-amino-1,2,4-triazol-5-yl)] phenylalanyl, [4-(3-amino-1,2,4-triazol-5-yl)]-N-methylphenylalanyl, (4-N-acetyl)-N-methylphenylalanyl, (4-N-acetyl)N-phenylalanyl, 1,2,3,4-tetrahydroisoquinoline-7-hydroxy-3-carbonyl, 1,2,3,4-tetrahydroisoquinoline-3-carbonyl, arginyl, sarcosyl, tyrosyl, and N-methyltyrosyl; or where B and C taken together form an amino acid derivative having the formula:

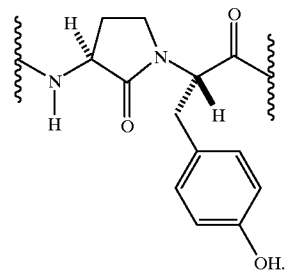

D is an amino acid residue selected from D-arginyl, D-citrullyl, glycyl, D-homocitrullyl, D-diethyl-homoarginyl, D-(N-epsilon-nicotinyl)lysyl, N-methylphenyl-alanyl, phenylalanyl, D-phenylalanyl, D-tryptyl, D-[4-(3-amino-1,2,4-triazol-5-yl)]-phenylalanyl, and D-(4-N-acetyl)-phenylalanyl.

E is an amino acid residue selected from cyclohexylalanyl, glycyl, leucyl, and N-methylleucyl; or where D and E taken together form an amino acid derivative having the formula:

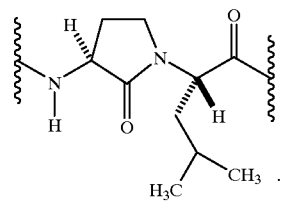

$R^1$ is selected from the group consisting of —NH(CH$_2$)—$R^2$, —NR$^3$—(CH$_2$)$_m$—NHR$^4$, —NH—(CH$_2$)$_n$—NR$^5$R$^6$, and —NH—(CH$_2$)$_p$—NH—C(=NH)—NH$_2$; wherein: l is 0–10, m is 1–2, n is 1–10, p is 1–10; $R^2$ is hydrogen, hydroxy, amino, amido, methyl, or phenyl; $R^3$ is hydrogen, methyl, or ethyl; $R^4$ is hydrogen, methyl, amino or amido; and $R^5$ and $R^6$ taken together with the nitrogen atom to which each is attached form an aromatic or non-aromatic ring, having at least one nitrogen atom, and selected from the group consisting of morpholinyl, piperidinyl, pyridyl, pyridinyl, pyrrolyl, pyrrolidinyl, pyrrolidinonyl, and quinuclidinyl.

Preferred compounds of the invention are of the formula (II), wherein:

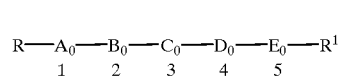
(II)

$A_0$ is selected from 3-(1-naphthyl)-D-alanyl, D-tryptyl, D-3-(4,4'-biphenyl)alanyl, and D-(benzthienyl)alanyl;

$B_0$ is seryl;

$C_0$ is an amino acid residue selected from N-methylphenylalanyl, (4-N-nitro)-N-methylphenylalanyl, [4-(3-amino-1,2,4-triazol-5-yl)] phenylalanyl, [4-(3-amino-1,2,4-triazol-5-yl)]-N-methylphenylalanyl, (4-N-acetyl)-N-methylphenylalanyl, (4-N-acetyl)-N-phenylalanyl, 1,2,3,4-tetrahydroisoquinoline-7-hydroxy-3-carbonyl, 1,2,3,4-tetrahydroisoquinoline-3-carbonyl, sarcosyl, tyrosyl, and N-methyltyrosyl; or where $B_0$ and $C_0$ taken together form an amino acid derivative having the formula:

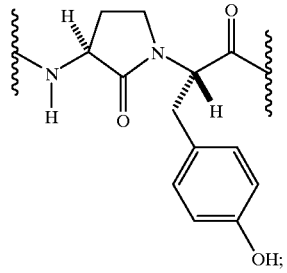

$D_0$ is an amino acid residue selected from glycyl, D-diethyl-homoarginyl, D-(N-epsilon-nicotinyl)lysyl, N-methylphenylalanyl, phenylalanyl, D-phenylalanyl, D-[4-(3-amino-1,2,4-triazol-5-yl)]-phenylalanyl, and D-(4-N-acetyl)-phenylalanyl; and $E_0$ is an amino acid residue selected from glycyl, leucyl, and N-methylleucyl; or where $D_0$ and $E_0$ taken together form an amino acid derivative having the formula:

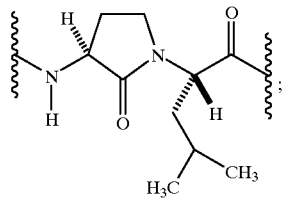

wherein R and R¹ are as previously defined.

In a preferred R group, X is selected from hydrogen and halide; Y is hydrogen; and n is 1–3. X is more preferably fluorine. A more preferred R group is 4-fluoro-phenylpropionyl (or 4-F-phenylpropionyl).

The preferred R¹ groups have the formula —NH—(CH₂)$_n$—NR⁵R⁶, wherein R⁵ and R⁶ taken together with the nitrogen atom to which each is attached form an aromatic or non-aromatic ring, having at least one nitrogen atom, which is preferably selected from the group consisting of morpholinyl, piperidinyl, pyridyl, pyridinyl, pyrrolyl, pyrrolidinyl, pyrrolidinonyl, and quinuclidinyl. It is preferred that the R¹ is of the formula —NH—(CH₂)$_n$—NR⁵R⁶, wherein n is 2 and —NR⁵R⁶ forms pyrrolidine, or —NH—CH₂—CH₂—(1-pyrrolidine).

The compounds provide LHRH analogs that exhibit LHRH antagonist properties.

Unless otherwise indicated by the "D" prefix, the stereochemistry of the alpha-carbon atom of the amino acids and aminoacyl residues in peptides described in this specification and the appended claims is the natural or "L" configuration.

As set forth above, the conventional abbreviations for the various common amino acids are used as generally accepted in the art and as recommended by the IUPAC-IUB Commission on Biochemical Nomenclature, *Biochemistry II*, 1726 (1972). These represent L-aminoacids, with the exception of the achiral amino acid glycine, and with the further exception of any unnatural or natural amino acids which are achiral, or otherwise designated as D-. All peptide sequences mentioned herein are written accordingly to the generally accepted convention whereby the N-terminal amino acid is on the left and the C-terminal amino acid is on the right. Further information on the nomenclature of peptides is described in *Pure Appl Chem.*, 56:595 (1984).

Other abbreviations which are useful in describing the invention are the following:

| Amino acids, protecting groups, reagents | Abbreviation |
|---|---|
| 3-(1-naphthyl)-D-alanyl | D1Nal |
| 3-(1-naphthyl)-alanyl | 1Nal |
| D-arginine | DArg |
| D-aspartic acid | DAsp |
| D-(benzthienyl)alanine | DBal |
| D-citrulline | DCit |
| Cyclohexylalanyl | Cha |
| D-glutamine | DGln |
| Glycine | Gly |
| D-homocitrulline | DHcit |
| D-diethyl-homoarginine | DHarg(Et₂) |
| Leucine | Leu |
| N-methylleucine | NMeLeu |
| (N-epsilon-nicotinyl)-lysine | Lys(Nic) |
| D-N-epsilon-nicotinyl)-lysine | DLys(Nic) |
| Phenylalanine | Phe |
| D-3-(4,4'-biphenyl)alanine | DBiphe |

-continued

| Amino acids, protecting groups, reagents | Abbreviation |
|---|---|
| [(3-amino-1,2,4-triazol-5-yl)]-N-phenylalanine | Phe(Atza) |
| (4-N-acetyl)-phenylalanine | Phe(4Nac) |
| D-[(4-amino-1,2,4-triazol-5-yl)]-N-phenylalanine | DPhe(4-Atza) |
| D-(4-N-acetyl)-phenylalanine | DPhe(4NAc) |
| (4-N-acetyl)-N-methylphenylalanine | NMePhe(4Nac) |
| N-methylphenylalanine | NMePhe |
| [4-(3-amino-1,2,4-triazol-5-yl)]-N-methylphenyl-alanine | NMePhe(4-Atza) |
| (4-N-nitro)-N-methylphenylalanine | NMePhe (4-NO₂) |
| Sarcosine | Sar |
| Serine | Ser |
| 1,2,3,4-tetrahydroisoquinoline-7-hydroxy-3-carbonyl | OHTic |
| 1,2,3,4-tetrahydroisoquinoline-3-carbonyl | Tic |
| Tyrosine | Tyr |
| N-methyltyrosine | NMeTyr |
| D-tryptophan | DTrp |

The compounds of the present invention are useful in modulating levels of gonadotropin and androgen secretion in mammals. The compounds are particularly useful for their activity as LHRH agonists or antagonists.

The term "pharmaceutically acceptable salt" as used herein refers to acid addition salts of a compound of the invention which are, within the scope of sound medical judgement, suitable for use in contact with the tissues of mammals, including humans arid lower animals, without undue toxicity, irritation, allergic response, and the like commensurate with a reasonable benefit/risk ratio, and which are effective for their intended use. Pharmaceutically acceptable salts are well known in the art, and are summarized in S. M. Berge, et al., *J Pharmaceutical Sciences* 66:1–19 (1977). The salts can be prepared in situ during the final isolation and purification of the compounds of the invention, or separately by reacting the free base function with a suitable organic acid. Examples of pharmaceutically acceptable, nontoxic acid addition salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalene-sulfonate, nicotinate, nitrate, oleate, oxalate, palmitate, palmoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, loweralkylsulfonate and aryl sulfonate.

The term "pharmaceutically acceptable ester" as used herein refers to non-toxic esters derived by the condensation of a compound of the invention with an alcohol. Examples of pharmaceutically acceptable, non-toxic esters of the compounds of the invention include $C_1$ to $C_6$ alkanoyl esters wherein the alkanoyl group is a straight or branched chain, such as formate, acetate, propanoate, butyrate, isopropanoate, pentanoate, hexanoate, and the like. Esters of the compounds of the present invention may be prepared according to conventional methods.

The term "pharmaceutically acceptable prodrug" as used herein refers to biolabile compounds or derivatives which, upon delivery or administration to a treatment subject, are converted to in vivo parent compounds of the invention. Prodrugs of compounds of the invention are suitable for use in contact with the tissues of mammals, including humans and lower animals, without undue toxicity, irritation, allergic response, and the like commensurate with a reasonable benefit/risk ratio as determined by one of ordinary skill in the medical arts within the scope of sound medical judgement, and which are effective for their intended use, as well as the zwitterionic forms, where possible, of the compounds of the invention. Prodrugs are well-known in the art, and generally refers to compounds that are rapidly transformed in vivo to yield the parent compounds of the invention, for example by hydrolysis in blood. A summary of the art is described in T. Higuchi and V. Stella, "Pro-drugs as Novel Delivery Systems," Vol. 14 of the A.C.S. Symposium Series and in *Bioreversible Carriers in Drug Design*, ed. Edward B. Roche, American Pharmaceutical Association and Pergamon Press, 1987. Such prodrugs are readily apparent to one of ordinary skill in the art and can be regarded as functional equivalents of the compounds of the invention.

Where appropriate, prodrugs of compounds of the present invention may be prepared by any suitable method. For those compounds in which the prodrug moiety is an amino acid or peptide functionality, the condensation of the amino group with amino acids and peptides may effected in accordance with conventional condensation methods such as the azide method, the mixed acid anhydride method, the DCC (dicyclohexylcarbodiimide) method, the active ester method (p-nitrophenyl ester method, N-hydroxysuccinic acid imide ester method, cyanomethyl ester method, and the like), the Woodward reagent K method, the DCC-HOBT (1-hydroxybenzotriazole) method and the like. Classical methods for amino acid condensation reactions are described in M. Bodansky, Y. S. Kausner and M. A. Ondetti, *Peptide Synthesis*, Second Edition, NY, 1976.

Representative examples of compounds contemplated as within the scope of the present invention include, but are not limited to the following:

4-F-Phenylpropionyl-D1Nal-Ser-NMeTyr-DLys(Nic)-Leu-NH—$(CH_2)_2$-(1-pyrrolidine);

4-F-Phenylpropionyl-D1Nal-Ser-NMeTyr-Gly-Leu-NH—$(CH_2)_2$-(1-pyrrolidine);

4-F-Phenylpropionyl-D1Nal-Ser-Sar-DLys(Nic)-Leu-NH—$(CH_2)_2$-(1-pyrrolidine);

4-F-Phenylpropionyl-D1Nal-Ser-Sar-DLys(Nic)-Gly-NH—$(CH_2)_2$-(1-pyrrolidine);

4-F-Phenylpropionyl-Gly-Ser-Sar-DLys(Nic)-Leu-NH—$(CH_2)_2$-(1-pyrrolidine);

4-F-Phenylpropionyl-D1Nal-Gly-NMeTyr-DLys(Nic)-Leu-NH—$(CH_2)_2$-(1-pyrrolidine);

4-F-Phenylpropionyl-D1Nal-Ser-Tyr-DLys(Nic)-Leu-NH—$(CH_2)_2$-(1-pyrrolidine);

4-F-Phenylpropionyl-D1Nal-Ser-NMeTyr-Gly-NMeLeu-NH—$(CH_2)_2$-(1-pyrrolidine);

4-F-Phenylpropionyl-D1Nal-Gly-NMeTyr-Gly-NMeLeu-NH—$(CH_2)_2$-(1-pyrrolidine);

4-F-Phenylpropionyl-DTrp-Ser-NMeTyr-DLys(Nic)-Leu-NH—$(CH_2)_2$-(1-pyrrolidine);

4-F-Phenylpropionyl-DBiphe-Ser-NMeTyr-DLys(Nic)-Leu-NH—$(CH_2)_2$-(1-pyrrolidine);

4-F-Phenylpropionyl-DBiphe-Ser-NMePhe-DLys(Nic)-Leu-NH—$(CH_2)_2$-(1-pyrrolidine);

4-F-Phenylpropionyl-DBiphe-Ser-OHTic-DLys(Nic)-Leu-NH—$CH_2)_2$-(1-pyrrolidine);

4-F-Phenylpropionyl-1Nal-Ser-NMeTyr-DLys(Nic)-Leu-NH—$(CH_2)_2$-(1-pyrrolidine);

4-F-Phenylpropionyl-DTrp-Ser-NMeTyr-DPhe-Leu-NH—$(CH_2)_2$-(1-pyrrolidine);

4-F-Phenylpropionyl-D1Nal-Pro-NMeTyr-DLys(Nic)-Leu-NH—$(CH_2)_2$-(1-pyrrolidine);

4-F-Phenylpropionyl-D1Nal-Ser-Tic-DLys(Nic)-Leu-NH—$(CH_2)_2$-(1-pyrrolidine);

4-F-Phenylpropionyl-D1Nal-Ser-NMeTyr-6,7[2-(S-3-amino-2-oxo-pyrrolidin-1-yl)-S-2-isopropylmethylacetyl]-NH—$(CH_2)_2$-(1-pyrrolidine);

4-F-Phenylpropionyl-D1Nal-6,7[2-(S-3-amino-2-oxo-pyrrolidin-1-yl)-S-2-(para-hydroxyl)phenylacetyl]-DLys(Nic)-Leu-NH—$(CH_2)_2$-(-pyrrolidine);

4-F-Phenylpropionyl-D1Nal-Ser-Lys(Nic)-DLys(Nic)-Leu-NH—$(CH_2)$2-(1-pyrrolidine);

4-F-Phenylpropionyl-D1Nal-Ser-NMeTyr-DCit-Leu-NH—$(CH_2)_2$-(1-pyrrolidine);

4-F-Phenylpropionyl-D1Nal-Ser-Arg-DTrp-Leu-NH—$(CH_2)_2$-(1-pyrrolidine);

4-F-Phenylpropionyl-D1Nal-Ser-NMeTyr-DArg-Leu-NH—$(CH_2)_2$-(1-pyrrolidine);

4-F-Phenylpropionyl-D1Nal-Ser-NMePhe(4-$NO_2$)-DCit-Leu-NH—$(CH_2)_2$-(1-pyrrolidine);

4-F-Phenylpropionyl-D1Nal-Ser-NMePhe(4-NAc)-DPhe(NAc)-Leu-NH—$(CH_2)_2$-(1-pyrrolidine);

4-F-Phenylpropionyl-D1Nal-Ser-NMePhe(4-Atza)-DPhe(4-Atza)-Leu-NH—$(CH_2)$2-(1-pyrrolidine);

4-F-Phenylpropionyl-D1Nal-Ser-Phe(4-Atza)-DPhe(4-Atza)-Leu-NH—$(CH_2)$2-(1-pyrrolidine);

4-F-Phenylpropionyl-D1Nal-Ser-NMeTyr-DLys(Nic)-Leu-N'-isp-aminoethyl amide;

4-F-Phenylpropionyl-D1Nal-Ser-NMeTyr-DLys(Nic)-Leu-guanidinobutyl amide;

4-F-Phenylpropionyl-D1Nal-Ser-NMeTyr-DLys(Nic)-Leu-N'-isp-aminopenthyl amide;

4-F-Phenylpropionyl-D1Nal-Ser-NMeTyr-DLys(Nic)-Leu-(3-quinuclidinyl amide);

4-F-Phenylpropionyl-D1Nal-Ser-NMeTyr-DLys(Nic)-Leu-aminoethyl amide;

4-F-Phenylpropionyl-D1Nal-Ser-NMeTyr-DLys(Nic)-Leu-aminobutyl amide; and

4-F-Phenylpropionyl-D1Nal-Ser-NMeTyr-DLys(Nic)-Leu-aminopentyl amide.

Another aspect of the present invention relates to pharmaceutical compositions comprising a compound of the present invention as the active ingredient and a pharmaceutically acceptable carrier. Pharmaceutically acceptable carriers suitable for the pharmaceutical compositions of the invention comprise non-toxic compatible substances useful for preparing a composition for administering the compound to a mammal in need of treatment.

Suitable pharmaceutically acceptable carriers generally include, but are not limited to, non-toxic, inert solid, semi-solid, or liquid filler, diluent, encapsulating material or formulation auxiliary of any type. Exemplary material which can serve as pharmaceutically acceptable carriers are sugars, such as lactose, glucose, and sucrose; starches, such as corn starch and potato starch; cellulose and its derivatives, such as sodium carboxymethylcellulose, ethylcellulose and cellulose acetate; powdered tragacanth; malt; gelatin; talc, excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol, and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible substances used in pharmaceutical formulations. Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the pharmaceutically acceptable composition.

In another aspect of the invention, the invention relates to a method of modulating gonadotropic hormones in a mammal comprising administering to a mammal in need of such treatment a therapeutically effective amount of a compound as previously defined. Conditions for which an amount of the compound may be effective can be described as resulting in excessive tissue swelling, precocious puberty, hormonal imbalance, and other related conditions. Exemplary known symptoms and conditions for which the compounds are useful in treating include, but are not limited to, benign prostate hypertrophy, dysmenorrhea, endometriosis, precocious puberty, prostate cancer, uterine fibroids, prostate necrosis, and other sex hormone dependent diseases. These compounds provide novel peptides for treatment regimens useful in treating such conditions.

Compounds of the invention are administered to a mammal in need of such treatment by any of a variety of routes depending on the specific end use. Generally, the means for administering the peptide to a mammal will be a method selected from treatments consisting of oral, parenteral, vaginal, rectal, buccal (including sublingual), transdermal, and intranasal administration. Parental routes of administration include, but are not limited to subcutaneously, intramuscularly, and intravenously. The exact method and route of administration can be determined by one of ordinary skill in the medical arts having knowledge and the ability to develop a reasoned judgment as to the form of treatment administered to the mammal in need of treatment.

The exact dose and regimen for administration may depend on a variety of any factors including, but not limited to, the need of the individual subject being treated, the type of treatment, the degree of affliction or need, and length and frequency of the treatment. Generally, dosage for the treatment is between about 0.01 and 10 milligram of the active ingredient per kilogram body weight per day. Preferably, in light of the general expediency of the treatment, the dose administered is from about 0.1 to about 5.0 mg/kg body weight per day. The administration may be accomplished in a single, daily administration or by distributing doses over several applications or by slow release in order to achieve the most effective results.

GENERAL PROCEDURE FOR PEPTIDE SYNTHESIS

Peptides of the present invention may be prepared by any techniques that are known to those skilled in the art. Commonly employed methods known in the art of peptide synthesis generally referred to as "solid phase" peptide synthesis, wherein sequential coupling of amino acids is accomplished attached to an inert solid support, and "solution phase" synthesis, the technique wherein amino acids are coupled in solution. Solid phase methods of synthesis on a support resin are described in J. M. Steward and J. D. Young, *Solid Phase Peptide Synthesis*, W. H. Freeman Co., San Francisco, 1963; and J. Meienhofer, *Hormonal Proteins and Peptides*, Vol. 2, p. 46, Academic Press (New York), 1973. Summary of classical solution phase synthesis techniques is recited in G. Schroder and K. Lupke, *The Peptides*, vol. 1, Academic Pressure (New York), 1965, and M. Bodansky, "The Practice of Peptide Synthesis" by M. Bodansky and A. Bodansky.

Starting materials used in these general methods of peptide synthesis comprise a suitable resin and one or more amino acids or derivatives thereof. Naturally occurring and commonly protected amino acids are commercially available or, alternatively, can be prepared with readily available starting materials by methods commonly known in the art.

In the solid support method, a solid support provides an inert surface to which an amino acid is attached. The solid support materials, typically resins, are inert to the reagents and reaction conditions of the peptide linkage formation as well as conditions for cleaving the final peptide from the solid support. Suitable solid supports useful for the above synthesis are chloromethylpolystyrene-divinylbenzene polymer, hydroxymethylpolystyrene-divinylbenzene polymer, benzyldrylaminopolystyrene-divinylbenzene polymer, and the like. Preferably, the support is chloromethylpolystyrene-1% divinylbenzene polymer.

Typically, the amino acid is protected or derivatized before attaching the amino acid to the resin. As used in the description of the general procedures for the peptide synthesis, the term "amino acid" refers to amino acids, salts, esters and derivatives thereof suitable for sequencing in a peptide synthesis as determined by one of ordinary skill in the art. The amino acid residues are attached to the resin or a formed polypeptide chain as a salt to synthesis the polypeptide chain having the desired sequence and having the desired length. Suitable salts of the amino acid are cesium, tetramethylammonium, triethyl-ammonium, 1,5-diazabicyclo-[5.4.0]undec-5-ene salts, or the like. Preferably, the amino acid is coupled with the solid support as a cesium salt.

Protecting groups preferred for preparing the peptides provide stable moieties for protecting the alpha-amino function of the amino acids. The protecting groups used generally have properties of being stable to conditions of peptide linkage formation and can be readily removed without destruction of the growing peptide chain or racemization of any of the chiral centers contained therein. Suitable protecting groups are selected from the group consisting of hydroxy protecting groups. Exemplary suitable protecting groups include, but are not limited to, t-butyloxycarbonyl (BOC), benzyloxycarbonyl (Cbz), biphenylisopropyloxycarbonyl, t-amyloxycarbonyl, isobornyloxycarbonyl, (alpha,alpha)-dimethyl-3,5dimethoxybenzyloxycarbonyl, o-nitrophenylsulfenyl, 2-cyano-t-butyloxy-carbonyl-9-fluoroenylmethyloxycarbonyl (FMOC), and the like. The preferred protecting group is t-butyloxycarbonyl.

Coupling of the protected amino acid to the support is accomplished in an inert solvent. Solvents suitable for the coupling reaction include, but are not limited to, ethanol, dichloromethane, methylene chloride, acetonitrile, N,N- dimethylformamide (DMF), and the like, or a mixture thereof. Preferably, the solvent is ethanol or dimethylformamide. Typically, the reaction is carried out between about 40° C. and 60° C., from about 12 to about 48 hours. The preferred reaction is accomplished in DMF at about 50° C. for about 24 hours.

Coupling of subsequent protected amino acid residues and derivatives can be accomplished using an automatic peptide synthesizer. These synthesizers are well-known in the art. Coupling of the attached amino acid and residue with additional amino acids involves reacting the attached amino acid with a suitable coupling reagent for about 1 to 24 hours. Suitable coupling reagents are selected from the group consisting of N,N'-dicyclohexylcarbodiimide or N,N'-diisopropylcarbodiimide (DIC) with or without 1-hydroxybenzotriazole (HOBT), benzotriazol-1-yloxy-tris(dimethylamino)phosphonium-hexafluorophosphate (BOP) and bis-(2-oxo-3-oxazolidinyl)phosphine chloride (BOPCl). Preferably, the reaction is carried out for 12 hours at a temperature of between 10° C. and 50° C. in the inert solvent. Each protected amino acid is introduced in 0.4 M concentration and approximately 3.5 molar excess. Preferably, the coupling reaction is carried out in a 1:1 mixture of dichloromethane and DMF at ambient temperatures.

Cleaving the polypeptide chain by aminolysis removes the final peptide chain from the solid support. Preferred cleaving reagents are alkylamines or fluoroalkylamines in the presence or absence of boron tribromide. The most preferred is 1-(2-aminoethyl)-pyrrolidine.

Deprotection is usually accomplished under anhydrous strong acidic conditions that remove the protecting groups without destroying the formed peptide chain or degrading the acid sensitive moieties present on the peptide chain. Suitable deprotecting agents are anhydrous liquid hydrogen fluoride in the presence of anisole and dimethylphosphite or other carbonium ion scavenger, hydrogen fluoride/pyridine complex, tris(trifluoroacetyl)-boron and trifluoroacetic acid, hydrogen and palladium on carbon on polyvinylpyrrolidone, sodium in liquid ammonia. Preferably, the deprotecting agent is liquid hydrogen fluoride in the presence of anisole and dimethylphosphite. Preferred temperatures for carrying out the deprotection reaction are from about −10° C. to about +10° C. The most preferred reaction is carried out at 0° C. for about 30 minutes.

Alternatively, the polypeptide is synthesized in solution by methods known to those with skill in the art. The methods are described in "The Practice of Peptide Synthesis" by M. Bodansky and A. Bodansky. Briefly, an amino acid is protected with a protecting group and is coupled to the next N-free amino acid using a suitable coupling reagent as described above at 0° C. to ambient temperatures for about 1 to about 5 hours to afford a dipeptide fragment. The peptide fragment is deprotected to afford a free amine terminus and a subsequent protected amino acid is coupled to the fragment under the coupling conditions previously described. Suitable reagents are described above in accordance with the solid peptide synthesis method.

An example of classical peptide solution synthesis is described in Example 1 of the following Examples.

Procedures of the invention can be better understood in accordance with the Examples. The Examples are meant to merely illustrate compounds and processes which can be carried out in accordance with the invention are not meant to be limiting in any way.

EXAMPLES

Example 1

4-F-Phenylpropionyl-D1Nal-Ser-NMeTyr-DLys(Nic)-Leu-NH—(CH$_2$)$_2$-(1-pyrrolidine)

In the reaction vessel of a Milligen-Biosearch 9500 peptide synthesizer was placed 10 g (0.42 mmol) of BOC-Leu-O-resin (Merrifield resin). Amino acids were added sequentially according to the following synthetic cycle:

1. Deblocking, to remove the t-BOC group from the alpha-amino function of the peptide, was carried out using a solution of 45% trifluoroacetic acid (TFA), 2.5% anisole, 2.0% dimethyl phosphite, and 50.5% methylene chloride. The resin was prewashed with the deblocking solution for one minute and then the deblocking reaction was run for 20 minutes.
2. Base wash, to remove and neutralize the TEA used for deprotection, was carried out using a solution of 10% N,N'-diisopropylethylamine in methylene chloride. The resin was washed with base three times for one minute each time after a deblocking step.
3. Coupling reaction was carried out using a 3-fold molar excess of 0.3 M DMF solution of a t-BOC protected amino acid derivative along with a 3-fold molar excess of 0.3 M methylene chloride solution of diisopropylcarbodiimide as activator. The activated amino acid was then coupled to the free alpha-amino group of the peptide-resin. The reaction time was as described in the synthesis protocol described below.
4. Wash, each reaction step was followed by three washes of one minute each: one of methylene chloride, one of (1:1) methylene chloride/DMF, and one of DMF.

Synthesis Protocol

The amino acids were coupled to the resin according to the following order, number and duration of couplings:

| # Amino acid | Coupling |
| --- | --- |
| 1. BOC-Leu | two-1h |
| 2. BOC-DLys(Nic) | two-1h |
| 3. BOC-NMeTyr(O-2,6-diClBzl) | two-1h |
| 4. BOC-Ser(OBzl) | two-1h |
| 5. BOC-D1Nal | two-1h |
| 6. 4-F-phenylpropionic acid | two-1h |

Upon completion of the synthesis the peptide-resin was dried overnight over P$_2$O$_5$ under vacuum. The peptide-resin (1 g) was then treated at room temperature with (1:1) anhydrous methylene chloride/benzene (10 ml) with stirring under N$_2$. To the slurry was added a 0.63 M solution of boron tribromide in methylene chloride (2 ml) and the mixture was stirred for one hour, then aminoethyl-N-pyrrolidine (0.3 ml) was added and stirring continued overnight. Methanol (1 ml) was added and the mixture was stirred for 15 min and filtered. The resin was washed thoroughly with methanol three times and the filtrate and washes were combined and concentrated in vacuo. The residue was dried in vacuo over P$_2$O$_5$ overnight and then treated with HF/anisole to remove protecting groups. After workup and lyophilization the crude product was purified by HPLC using C-18 reverse phase column and running a gradient of 25–50%, over 30 minutes, of acetonitrile/water containing 0.1% trifluoroacetic acid. The desired compound, 4-F-phenylpropionyl-D1Nal-Ser-NMeTyr-DLys(Nic)-Leu-NH—(CH$_2$)$_2$-(1-pyrrolidine), was obtained as trifluoroacetate salt: R$_t$=27.0 min; FAB Mass spec for C$_{59}$H$_{75}$N$_9$O$_9$F showed (M+H) @ 1072 m/z; Amino Acid Anal.: 0.36 Ser; 0.85 NMeTyr; 1.01 Leu; 0.99 Lys.

Example 2

4-F-Phenylpropionyl-D1Nal-Ser-NMeTyr-Gly-Leu-NH—(CH$_2$)$_2$-(1pyrrolidine)

The procedure described in Example 1 was used, but substituting BOC-Gly for BOC-DLys(Nic). After cleavage of the peptide from the resin, removal of the protecting groups with HF and HPLC purification and lyophilization the desired product, 4-F-Phenylpropionyl-D1Nal-Ser-NMeTyr-Gly-Leu-NH—(CH$_2$)$_2$-(1-pyrrolidine), was obtained as trifluoroacetate salt: R$_t$=27.3 min; FAB Mass spec for C$_{49}$H$_{62}$N$_7$O$_8$F showed (M+H) @ 896 m/z; Amino Acid Anal.: 0.41 Ser; 0.98 Gly; 1.11 NMeTyr; 1.00 Leu; 0.98 Lys.

Example 3

4-F-Phenylpropionyl-D1Nal-Ser-Sar-DLys(Nic)-Leu-NH—(CH$_2$)$_2$(1-pyrrolidine)

The procedure described in Example 1 was used, but substituting BOC-Sar for BOC-NMeTyr(OBzl)). After cleavage of the peptide from the resin, removal of the protecting groups with HF and HPLC purification and lyophilization the desired product, 4-F-Phenylpropionyl-D1Nal-Ser-Sar-DLys(Nic)-Leu-NH—(CH$_2$)$_2$-(1-pyrrolidine), was obtained as trifluoroacetate salt: R$_t$=22.6 min; FAB Mass spec for C$_{52}$H$_{67}$N$_9$O$_8$F showed (M+H) @ 966 m/z, Amino Acid Anal.: 0.39 Ser; 0.98; 1.00 Leu; 1.10 Lys.

Example 4

4-F-Phenylpropionyl-D1Nal-Ser-Sar-DLys(Nic)-Gly-NH—(CH$_2$)$_2$-(1-pyrrolidine)

The procedure described in Example 1 was used, but substituting BOC-Gly for BOC-Leu. After cleavage of the peptide from the resin, removal of the protecting groups with HF and HPLC purification and lyophilization the desired product, 4-F-Phenylpropionyl-D1Nal-Ser-Sar-DLys(Nic)-Gly-NH—(CH$_2$)$_2$-(1-pyrrolidine), was obtained as trifluoroacetate salt: R$_t$=20.8 min; FAB Mass spec for C$_{55}$H$_{66}$N$_9$O$_9$F showed (M+H) @ 1017 m/z; Amino Acid Anal.: 0.41 Ser; 0.98 Gly; 1.01 NMeTyr; 1.10 Lys.

Example 5

4-F-Phenylpropionyl-Gly-Ser-Sar-DLys(Nic)-Leu-NH—(CH$_2$)$_2$-(1-pyrrolidine)

The procedure described in Example 1 was used, but substituting BOC-Gly for BOC-D1Nal. After cleavage of the peptide from the resin, removal of the protecting groups with HF and HPLC purification and lyophilization the desired product, 4-F-Phenylpropionyl-Gly-Ser-Sar-DLys(Nic)-Leu-NH—(CH$_2$)$_2$-(1-pyrrolidine), was obtained as trifluoroacetate salt: R$_t$=12.4 min; FAB Mass spec for C$_{48}$H$_{66}$N$_9$O$_9$F showed (M+H) @ 932 m/z; Amino Acid Anal.: 0.49 Ser; 1.01 Gly; 0.88 NMeTyr; 1.00 Leu; 0.97 Lys.

Example 6

4-F-Phenylpropionyl-D1Nal-Gly-NMeTyr-DLys(Nic)-Leu-NH—(CH$_2$)$_2$-(1-pyrrolidine)

The procedure described in Example 1 was used, but substituting BOC-Gly for BOC-Ser(OBzl). After cleavage of the peptide from the resin, removal of the protecting groups with HF and HPLC purification and lyophilization the desired product, 4-F-Phenylpropionyl-D1Nal-Gly-NMeTyr-DLys(Nic)-Leu-NH—(CH$_2$)$_2$-(1-pyrrolidine), was obtained as trifluoroacetate salt: R$_t$=26.8 min; FAB Mass spec for C$_{58}$H$_{72}$N$_9$O$_8$F showed (M+H) @ 1042 m/z; Amino Acid Anal.: 1.00 Gly; 1.05 NMeTyr 0; 0.99 Leu; 0.96 Lys.

Example 7

4-F-Phenylpropiopyl-D1Nal-Ser-Tyr-DLys(Nic)-Leu-NH—(CH$_2$)$_2$-(1-pyrrolidine)

The procedure described in Example 1 was used, but substituting BOC-Tyr(OBzl) for BOC-NMeTyr(OBzl). After cleavage of the peptide from the resin, removal of the protecting groups with HF and HPLC purification and lyophilization the desired product, 4-F-Phenylpropionyl-D1Nal-Ser-Tyr-DLys(Nic)-Leu-NH—(CH$_2$)$_2$-(1-pyrrolidine), was obtained as trifluoroacetate salt: R$_t$=24.9 min; FAB Mass spec for C$_{58}$H$_{72}$N$_9$O$_9$F showed (M+H) @ 1057 m/z; Amino Acid Anal.: 0.38 Ser; 0.95 Tyr; 1.00 Leu; 0.96 Lys.

Example 8

4-F-Phenylpropionyl-D1Nal-Ser-NMeTyr-Gly-NMeLeu-NH—(CH$_2$)$_2$-(1Pyrrolidine)

The procedure described in Example 1 was used, but substituting BOC-Gly and BOC-NMeLeu for BOC-DLys(Nic) and BOC-Leu, respectively. After cleavage of the peptide from the resin, removal of the protecting groups with HF and HPLC purification and lyophilization the desired product, 4-F-Phenylpropionyl-D1Nal-Ser-NMeTyr-Gly-NMeLeu-NH—(CH$_2$)$_2$-(I-pyrrolidine), was obtained as trifluoroacetate salt: R$_t$=30.0 min; FAB Mass spec for C$_{50}$H$_{64}$N$_7$O$_8$F showed (M+H) @ 909 m/z; Amino Acid Anal.: 0.49 Ser; 1.2 Gly; 1.02 NMeTyr; 1.10 NMeLeu.

Example 9

4-F-Phenylpropionyl-D1Nal-Gly-NMeTyr-Gly-NMeLeu-NH—(CH$_2$)$_2$-(1-pyrrolidine)

The procedure described in Example 8 was used, but substituting BOC-Gly for BOC-Ser(OBzl). After cleavage of the peptide from the resin, removal of the protecting groups with HF and HPLC purification and lyophilization the desired product, 4-F-Phenylpropionyl-D1Nal-Gly-NMeTyr-Gly-NMeLeu-NH—(CH$_2$)$_2$-(1-pyrrolidine), was obtained as trifluoroacetate salt: R$_t$=30.6 min; FAB Mass spec for C$_{49}$H$_{62}$N$_7$O$_7$F showed (M+H) @ 880 m/z; Amino Acid Anal.: 2.1 Gly; 0.99 NMeTyr; 1.00 Leu.

Example 10

4-F-Phenylpropionyl-DTrp-Ser-NMeTyr-DLys(Nic)-Leu-NH—(CH$_2$)$_2$-(1-pyrrolidine)

The procedure described in Example 1 was used, but substituting BOC-Trp for BOC-D1Nal. After cleavage of the peptide from the resin, removal of the protecting groups with HF and HPLC purification and lyophilization the desired product, 4-F-Phenylpropionyl-DTrp-Ser-NMeTyr-DLys(Nic)-Leu-NH—(CH$_2$)$_2$-(1-pyrrolidine), was obtained as trifluoroacetate salt: R$_t$=18.0 min; FAB Mass spec for C$_{57}$H$_{73}$N$_{10}$O$_9$F showed (M+H) @ 1061 m/z; Amino Acid Anal.: 0.48 Ser; 0.92 NMeTyr; 1.00 Leu; 0.96 Lys.

Example 11

4-F-Phenylpropionyl-DBiphe-Ser-NMeTyr-DLys(Nic)-Leu-NH—(CH$_2$)$_2$-(1-pyrrolidine)

The procedure described in Example 1 was used, but substituting BOC-Biphe for BOC-D1Nal. After cleavage of the peptide from the resin, removal of the protecting groups with HF and HPLC purification and lyophilization the desired product, 4-F-Phenylpropionyl-DBiphe-Ser-NMeTyr-DLys(Nic)-Leu-NH—(CH$_2$)$_2$-(1-pyrrolidine), was obtained as trifluoroacetate salt: R$_t$=28.2 min; FAB Mass spec for C$_{61}$H$_{76}$N$_9$O$_9$F showed (M+H) @ 1098 m/z; Amino Acid Anal.: 0.34 Ser; 1.01 NMeTyr; 1.00 Leu; 0.99 Lys.

Example 12

4-F-Phenylpropionyl-DBiphe-Ser-NMePhe-DLys(Nic)-Leu-NH—(CH$_2$)$_2$-( 1-pyrrolidine)

The procedure described in Example 1 was used, but substituting BOC-NMePhe for BOC-NMeTyr(OBzl). After cleavage of the peptide from the resin, removal of the protecting groups with HF and HPLC purification and lyophilization the desired product, 4-F-Phenylpropionyl-DBiphe-Ser-NMePhe-DLys(Nic)-Leu-NH—$(CH_2)_2$-(1-pyrrolidine), was obtained as trifluoroacetate salt: $R_t$=29.6 min; FAB Mass spec for $C_{59}H_{74}N_9O_8F$ showed (M+H) @ 1056 m/z; Amino Acid Anal.: 0.42 Ser; 1.00 Leu; 0.98 Lys.

Example 13

4-F-Phenylpropionyl-DBiphe-Ser-OHTic-DLys (Nic)-Leu-NH—$(CH_2)_2$-(1-pyrrolidine)

The procedure described in Example 1 was used, but substituting BOC-OHTic for BOC-NMeTyr(OBzl). After cleavage of the peptide from the resin, removal of the protecting groups with HF and HPLC purification and lyophilization the desired product, 4-F-Phenylpropionyl-DBiphe-Ser-OHTic-DLys(Nic)-Leu-NH—$(CH_2)_2$-(1-pyrrolidine), was obtained as trifluoroacetate salt: $R_t$=26.6 min; FAB Mass spec for $C_{59}H_{72}N_9O_9F$ showed (M+H) @ 1070 m/z; Amino Acid Anal.: 0.38 Ser; 1.00 Leu; 1.00 Lys.

Example 14

4-F-Phenylpropionyl-1Nal-Ser-NMeTyr-DLys(Nic)-Leu-NH—$(CH_2)_2$-(1-pyrrolidine)

The procedure described in Example 1 was used, but substituting BOC-1Nal for BOC-D1Nal. After cleavage of the peptide from the resin, removal of the protecting groups with HF and HPLC purification and lyophilization the desired product, 4-F-Phenylpropionyl-1Nal-Ser-NMeTyr-DLys(Nic)-Leu-NH—$(CH_2)_2$-(1-pyrrolidine), was obtained as trifluoroacetate salt: $R_t$=23.3 min; FAB Mass spec for $C_{59}H_{74}N_9O_9F$ showed (M+H) @ 1072 m/z; Amino Acid Anal.: 0.41 Ser; 1.00 Leu; 0.97 Lys.

Example 15

4-F-Phenylpropionyl-DTrp-Ser-NMeTyr-DPhe-Leu-NH—$(CH_2)_2$-(1-pyrrolidine)

The procedure described in Example 1 was used, but substituting BOC-DTrp and BOC-DPhe for BOC-D1Nal and BOC-DLys(Nic), respectively. After cleavage of the peptide from the resin, removal of the protecting groups with HF and HPLC purification and lyophilization the desired product, 4-F-Phenylpropionyl-DTrp-Ser-NMeTyr-DPhe-Leu-NH—$(CH_2)_2$-(1-pyrrolidine), was obtained as trifluoroacetate salt: $R_t$=23.3 min; FAB Mass spec for $C_{54}H_{67}N_8O_8F$ showed (M+H) @ 975 m/z; Amino Acid Anal.: 0.44 Ser; 0.96 NMeTyr; 1.00 Leu.

Example 16

4-F-Phenylpropionyl-D1Nal-Pro-NMeTyr-DLys (Nic)-Leu-NH—$(CH_2)_2$-(1-Pyrrolidine)

The procedure described in Example 1 was used, but substituting BOC-Pro for BOC-Ser(OBzl). After cleavage of the peptide from the resin, removal of the protecting groups with HF and HPLC purification and lyophilization the desired product, 4-F-Phenylpropionyl-D1Nal-Pro-NMeTyr-DLys(Nic)-Leu-NH—$(CH_2)_2$-(1-pyrrolidine), was obtained as trifluoroacetate salt: $R_t$=26.1 min; FAB Mass spec for $C_{61}H_{76}N_9O_8F$ showed (M+H) @ 1082 m/z; Amino Acid Anal.: 0.87 Pro; 0.99 NMeTyr; 1.00 Leu; 0.96 Lys.

Example 17

4-F-Phenylpropionyl-D1Nal-Ser-Tic-DLys(Nic)-Leu-NH—$(CH_2)_2$-(1-pyrrolidine)

The procedure described in Example 1 was used, but substituting BOC-Tic for BOC-NMeTyr(OBzl). After cleavage of the peptide from the resin, removal of the protecting groups with HF and HPLC purification and lyophilization the desired product, 4-F-Phenylpropionyl-D1Nal-Ser-Tic-DLys(Nic)-Leu-NH—$(CH_2)_2$-(1-pyrrolidine), was obtained as trifluoroacetate salt: $R_t$=27.1 min; FAB Mass spec for $C_{59}H_{72}N_9O_8F$ showed (M+H) @ 1054 m/z; Amino Acid Anal.: 0.37 Ser; 1.00 Leu; 0.99 Lys.

Example 18

Preparation of Enantiomers

4-F-Phenylpropionyl-D1Nal-Ser-NMeTyr-6,7[2-(S-3-amino-2-oxo-pyrrolidin-1-yl)-S-2-isopropylmethylacetyl]-NH—$(CH_2)_2$-(1-pyrrolidine) (enantiomer A and enantiomer B)

A solution of 4-F-phenylpropionyl-Ser(OBzl)-NMeTyr (O-2,6ClBzl)-OH (0.2 g), synthesized by conventional solution peptide synthesis methods, as described in "The Practice of Peptide Synthesis" by Bodansky M. and Bodansky A., in methylene chloride (8 ml) was cooled to 0° C. To the cold solution was added methyl 6,7-[2-(S-3-Amino-2-oxo-pyrrolidin-1-yl)]-S-2-isopropylmethylacetate (0.05 g) followed by 1,3-dicyclo-hexylamine carbodiimide (0.067 g). The solution was stirred for 1 hr at 0° C. and then at room temperature overnight. The reaction mixture was concentrated in vacuo and the residue was dissolved in ethyl acetate and the solution was washed with sodium bicarbonate solution, followed by 0.5 M citric acid wash and brine. The organic extracts were dried over anhydrous sodium sulfate and concentrated in vacuo to give crude methyl 4-F-phenylpropionyl-Ser(OBzl)-NMeTyr(O-2,6ClBzl)-6,7-(2-(S-3-Amino-2-oxo-pyrrolidin-1-yl))-S-2-isopropylmethylacetate, which by FAB Mass spec for $C_{60}H64N_5O_9Cl_2F$ showed (M+H) @ 1088 m/z. This compound was purified by HPLC using the same system described in Experiment 1.

Two enantiomers of methyl 4-F-phenylpropionyl-Ser (OBzl)-NMeTyr (O-2,6ClBzl)-6,7[2-(S-3-Amino-2-oxo-pyrrolidin-1-yl)]-S-2-isopropylmethylacetate were obtained: enantiomer A (0.036 g) and enantiomer B (0.028 g). Each enantiomer was separately dissolved in methylene chloride (1.5 ml) and treated at room temperature with aminoethylpyrrolidine (0.10 ml). The solutions were stirred for four days and then concentrated in vacuo. FAB Mass spec of each crude compound showed (M+H) @ 1170 m/z for $C_{60}H_{64}N_5O_9Cl_2F$. Each enantiomer was dried overnight over $P_2O_5$ and treated with anhydrous HF at 0° C. for 1 hr. The excess of reagent was removed in vacuo and the residue was washed with ether and then dissolved in (1:1) water/acetonitrile and lyophilized. Each crude enantiomer was purified by HPLC using the same conditions described above to give as trifluoroacetate salt:

Enantiomer A

4-F-Phenylpropionyl-D1Nal-Ser-NMeTyr-6,7[2-(S-3-amino-2-oxo-pyrrolidin-1-yl)-S-2-isopropylmethylacetyl]-NH—$(CH_2)_2$-(1-pyrrolidine): $R_t$=31.2min; FAB Mass spec for $C_{51}H_{64}N_7O_8F$ showed (M+H) @ 922 m/z; Amino Acid Anal.: 0.39 Ser; 0.93 NMeTyr.

Enantiomer B

4-F-Phenylpropionyl-D1Nal-Ser-NMeTyr-6,7[2-(S-3-amino-2-oxo-pyrrolidin-1-yl)-S-2-isopropylmethylacetyl]-NH—$(CH_2)_2$-(1-pyrrolidine) (enantiomer B): $R_t$=31.9 min; FAB Mass spec for $C_{51}H_{64}N_7O_8F$ showed (M+H) @ 922 m/z; Amino Acid Anal.: 0.41 Ser; 0.91 NMeTyr.

Example 19

4-F-Phenylpropionyl-D1Nal-6,7[2-(S-3-amino-2-oxo-pyrrolidin-1-yl)-S-2-(para-hydroxyl) phenylacetyl]-DLys(Nic)-Leu-NH—$(CH_2)_2$-(1-pyrrolidine)

4-F -Phenylpropionyl-D1Nal-6,7[2-(S-3-amino-2-oxo-pyrrolidin-1-yl)-S-2-(para-hydroxyl)phenylacetyl]-DLys (Nic)-Leu-NH—(CH$_2$)$_2$-(1-pyrrolidine) was prepared using solution synthesis according to the following Steps (a)–(d).

Step (a): BOC-Met-Tyr(O-2,6ClBzl)-OMe

To a solution of BOC-Met (11.4 g) in methylene chloride (200 ml) cooled to 0° C. was added H-Tyr(O-2,6ClBzl)-OMe (16.4 g) and 1,3-dicyclocarbodiimide (10.46 g). The solution was stirred at 0° C. for 1 hr and at room temperature overnight. The precipitate was filtered and the filtrate was washed three times with sodium bicarbonate, followed by citric acid and brine. The organic phase was dried over sodium sulfate and concentrated in vacuo to give the dipeptide as a white solid; FAB Mass spec for C$_{27}$H$_{34}$N$_2$O$_6$SCl$_2$ showed (M+H) @ 585 m/z.

Step (b): Sulfonium salt of BOC-Met-Tyr(O2,6ClBzl)-OMe

BOC-Met-Tyr(O-2,6ClBzl)-OMe (10.89 g) was treated with iodomethane (75 ml). The solution was stirred at room temperature overnight. The reaction mixture was concentrated in vacuo and the residue was washed with methylene chloride to give the sulfonium salt as solid foam. This was used in the next step without further purification.

Step (c): Methyl BOC-[2-3-Amino-2-oxo-pyrrolidin-1-yl)-S-2-(para-O-(2,6-diCl)Bzl)phenylacetate A solution of of BOC-Met-Tyr(O-2,6ClBzl)-OMe sulfonium salt (15.0 g) in (1:1) DMF/methylene chloride (310 ml) was treated portionwise at 0° C. with 60% dispersion of sodium hydride in mineral oil (1.4 g). The reaction mixture was stirred for 6 hr. Methyl acetate (150 ml) and water (2 ml) were carefully added and the reaction mixture was stirred at room temperature overnight. The reaction mixture was concentrated in vacuo and the residue was partitioned between methylene chloride, was acidified to pH 4 with citric acid and extracted with methylene chloride three times. The organic phase was dried and concentrated in vacuo. The crude product was purified by silica gel column chromatography eluting with (98:2) methylene chloride/methanol to give methyl BOC-(2-3-amino-2-oxo-pyrrolidin-1-yl)-S-2-(para-O-(2,6-diCl)Bzl)phenylacetate (2.15 g); FAB Mass spec for C$_{26}$H$_{30}$N$_2$O$_6$Cl$_2$ showed (M+K) @ 575 m/z.

Step (d): BOC-(2-3-Amino-2-oxo-pyrrolidin-1-yl)-S-2-(para-O-(2,6-diCl-Bzl)-phenylacetic acid A solution of lithium hydroxide monohydrate (0.23 g) in water (16 ml) was added with stirring to a solution of methyl BOC-(2-3-amino-2-oxo-pyrrolidin-1-yl)-S-2-(para-O-(2,6-diCl)Bzl)phenylacetate (2.15 g) in p- dioxane (24 ml) cooled to 0° C. The reaction mixture was stirred for 3.5 hr at 0° C. and then concentrated in vacuo. The residue was dissolved in methylene chloride and washed with 0.1 M HCl followed by brine, dried and concentrated in vacuo to give BOC-(2-3-Amino-2-oxo-pyrrolidin-1-yl)-S-2-(para-O-(2,6-diCl-Bzl)phenylacetic acid (1.83 g). This compound was used in the next step using solid phase synthesis of the whole peptide. The procedure described in Example 1 was used, but substituting give BOC-(2-3-amino-2-oxo-pyrrolidin-1-yl)-S-2-(para-O-(2,6-diCl-Bzl)phenylacetic acid for BOC-Ser(OBzl) and BOC-NMeTyr(O-2,6-Cl-Bzl). After cleavage of the peptide from the resin with aminoethylpyrrolidine, cleavage of the protecting group with HF, lyophilization and purification of the product by HPLC the product 4-F-Phenylpropionyl-D1Nal-6,7(2-(S-3-amino-2-oxo-pyrrolidin-1-yl)-S-2-(para-hydroxyl)phenylacetyl)-DLys(Nic)-Leu-NH—(CH$_2$)$_2$-(1-pyrrolidine) was obtained: R$_t$=23.7 min; FAB Mass spec for C$_{59}$H$_{72}$N$_9$O$_8$F showed (M+H) @ 1054 m/z; Amino Acid Anal.: 1.00 Leu; 0.94 Lys.

Example 20

The procedure described in Example 1 is used, but substituting the appropriate protected amino acids in the solid phase synthesis the following compounds are obtained:

4-F-Phenylpropionyl-D1Nal-Ser-Lys(Nic)-DLys(Nic)-Leu-NH—(CH$_2$)$_2$-(1-pyrrolidine)

4-F-Phenylpropionyl-D1Nal-Ser-NMeTyr-DCit-Leu-NH—(CH$_2$)$_2$-(1-pyrrolidine)

4-F-Phenylpropionyl-D1Nal-Ser-Arg-DTrp-Leu-NH—(CH$_2$)$_2$-(1-pyrrolidine)

4-F-Phenylpropionyl-D1Nal-Ser-NMeTyr-DArg-Leu-NH—(CH$_2$)$_2$—(l-pyrrolidine)

4-F-Phenylpropionyl-D1Nal-Ser-NMePhe(4-NO$_2$)-DCit-Leu-NH—(CH$_2$)$_2$-(1-pyrrolidine)

4-F-Phenylpropionyl-D1Nal-Ser-NMePhe(4NAc)-DPhe(NAc)-Leu-NH—(CH$_2$)$_2$-(1-pyrrolidine)

Example 21

4-F-Phenylpropionyl-D1Nal-Ser-NMePhe(4-Atza)-DPhe(4-Atza)-Leu-NH—(CH$_2$)$_2$-(1-pyrrolidine)

The procedure described in Example 1 is used, but substituting BOC-NMePhe-(4-N-FMOC) and BOC-DPhe(4-N-FMOC) for BOC-NMeTyr(O-2,6-diClBzl) and BOC-DLys(Nic) respectively. After the completion of the synthesis the peptide resin is treated with 30% piperidine/DMF for 2 to 24 hr to cleave the FMOC group from the 4-amino group on the phenyl rings of the side chains. The peptide resin is washed 3 times with methylene chloride, 3 times with DMF and reacted with 10 to 20-fold excess of diphenylcyanocarbodiimidate in DMF overnight, washed 3 times with methylene chloride, 3 times with DMF, and then reacted with 20- to 30-fold excess of hydrazine in DMF overnight. The peptide-resin is again washed, as previously described, dried over P$_2$O$_5$ overnight and then treated at room temperature with anhydrous methylene chloride (10 ml) with stirring under N$_2$. To the slurry is added a 0.63 M solution of boron tribromide in methylene chloride (2 ml) and the mixture is stirred for one hr, then aminoethyl-N-pyrrolidine (0.3 ml) is added and stirring is continued overnight. Methanol is added and the mixture is stirred for 15 min. and filtered. The resin is washed thoroughly with methanol three times and the filtrate the washes are combined and concentrated in vacuo. The residue is dried in vacuo over P$_2$O$_5$ overnight and the treated with HF/anisole to remove protecting groups. After workup and lyophilization the crude product is purified by HPLC to give the desired product 4-F-Phenylpropionyl-D1Nal-Ser-NMePhe(4-Atza)-DPhe(4-Atza)-Leu-NH—(CH$_2$)$_2$-(1-pyrrolidine).

Example 22

4-F-Phenylpropionyl-D1Nal-Ser-Phe(4-Atza-DPhe(4-Atza)-Leu-NH—(CH$_2$)$_2$-(1-pyrrolidine)

The procedure described in Example 21 is used, but substituting BOC-Phe-(4-N-FMOC) BOC-NMePhe(4-N-FMOC). After workup and lyophilization the crude product is purified by HPLC to give the desired product 4-F-Phenylpropionyl-D1Nal-Ser-Phe(4-Atza)-DPhe(4-Atza)-Leu-NH—(CH$_2$)$_2$-(1-pyrrolidine).

Example 23

The procedure described in Example 1 is used, but substituting aminoethyl-N-pyrrolidine with the appropriate amines the follwing compounds are obtained:

4-F-Phenylpropionyl-D1Nal-Ser-NMeTyr-DLys(Nic)-Leu-N'-isp-aminoethyl amide
4-F-Phenylpropionyl-D1Nal-Ser-NMeTyr-DLys(Nic)-Leu-guanidinobutyl amide
4-F-Phenylpropionyl-D1Nal-Ser-NMeTyr-DLys(Nic)-Leu-N'-isp-aminopenthyl amide
4-F-Phenylpropionyl-D1Nal-Ser-NMeTyr-DLys(Nic)-Leu-(3-quinuclidinyl amide)
4-F-Phenylpropionyl-D1Nal-Ser-NMeTyr-DLys(Nic)-Leu-aminoethyl amide
4-F-Phenylpropionyl-D1Nal-Ser-NMeTyr-DLys(Nic)-Leu-aminobutyl amide
4-F-Phenylpropionyl-D1Nal-Ser-NMeTyr-DLys(Nic)-Leu-aminopentyl amide

LHRH ANTAGONIST ACTIVITY

Representative compounds of the present invention were evaluated in vitro for inhibition of LH release from rat pituitary cells ($pA_2$). Methods for the assay procedures are described by F. Haviv, et al. *J. Med. Chem.*, 32:2340–2344 (1989). Values of $pA_2$ are the negative logarithms of the concentration of the particular antagonist test compound required to shift the response curve produced by the agonist leuprolide to two-fold higher concentration. Typically values of 6.0 or greater are indicative of good LHRH antagonist potency, with values of 7.0 or greater being preferred. Leuprolide LHRH agonist, disclosed and claimed in U.S. Pat. No. 4,005,063, has the structure 5-oxo-Pro$^1$-His$^2$-Tip$^3$-Ser$^4$-Tyr$^5$-D-Leu$^6$-Leu$^7$-Arg$^8$-Pro$^9$-NHEt.

Results for the assay of representative compounds in accordance with the invention are summarized in Table 1.

TABLE 1

| Example No. | LHRH Antagonist Activity ($pA_2$) |
|---|---|
| 1 | 9.91 |
| 2 | 9.14 |
| 3 | 7.66 |
| 4 | 7.82 |
| 5 | 6.18 |
| 6 | 8.90 |
| 7 | 9.73 |
| 8 | 9.00 |
| 9 | 7.72 |
| 10 | 8.69 |
| 11 | 7.62 |
| 12 | 9.54 |
| 13 | 9.40 |
| 14 | 8.68 |

TABLE 1-continued

| Example No. | LHRH Antagonist Activity ($pA_2$) |
|---|---|
| 15 | 8.59 |
| 16 | 8.71 |
| 17 | 9.32 |
| 18A | 8.46 |
| 18B | 9.86 |
| 19 | 7.89 |

What is claimed is:
1. A compound of the formula:

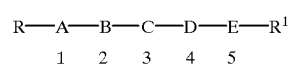

(I)

or a pharmaceutically acceptable salt, ester, or prodrug thereof, wherein:
R is of the formula:

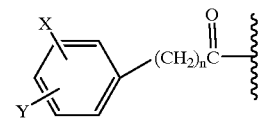

wherein X is hydrogen, lower alkyl, alkoxy, or a halide selected from the group consisting of bromide, chloride, fluoride, and iodide; Y is hydrogen or lower-alkyl; and n is 1–3;
A is an amino acid residue selected from the group consisting of:
3-(1-naphthyl)-D-alanyl,
3-(1-naphthyl)-L-alanyl,
D-tryptyl,
D-3-(4,4'-biphenyl)alanyl
D-(benzthienyl)alanyl, and
glycyl;
B is seryl or glycyl;
C is an amino acid residue selected from the group consisting of:
(N-epsilon-nicotinyl)lysyl,
N-methylphenylalanyl,
(4-N-nitro)-N-methylphenylalanyl,
[4-(3-amino-1,2,4-triazol-5-yl)]phenylalanyl,
[4-(3-amino-1,2,4-triazol-5-yl)]-N-methylphenylalanyl, (4-N-acetyl)-N-methylphenylalanyl,
(4-N-acetyl)-N-phenylalanyl,
1,2,3,4-tetrahydroisoquinoline-7-hydroxy-3-carbonyl
1,2,3,4-tetrahydroisoquinoline-3-carbonyl
arginyl,
sarcosyl,
tyrosyl, and
N-methyltyrosyl;
or where B and C taken together form an amino acid derivative having the formula:

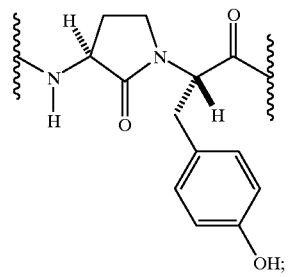

D is an amino acid residue selected from the group consisting of:
D-arginyl,
D-citrullyl,
glycyl,
D-homocitrullyl,
D-diethyl-homoarginyl,
D-(N-epsilon-nicotinyl)lysyl,
N-methylphenylalanyl,
phenylalanyl,
D-phenylalanyl,
D-tryptyl,
D-[4-(3-amino-1,2,4-triazol-5-yl)]-phenylalanyl, and
D-(4-N-acetyl)-phenylalanyl;
E is an amino acid residue selected from the group consisting of:
cyclohexylalanyl,
glycyl,
leucyl, and
N-methylleucyl;
or where D and E taken together form an amino acid derivative having the formula:

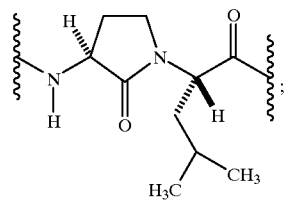

$R_1$ is selected from the group consisting of
—NH(CH$_2$)$_l$R$^2$, —NR$^3$—(CH$_2$)$_m$—NHR$^4$, —NH—(CH$_2$)$_n$—NR$^5$R$^6$ and —NH—(CH$_2$)$_p$—NH—C(=NH)—NH$_2$; wherein:
l is 0–10, m is 1–2, n is 1–10, p is 1–10;
R$^2$ is hydrogen, hydroxy, amino, amido, methyl, or phenyl;
R$^3$ is hydrogen, methyl, or ethyl;
R$^4$ is hydrogen, methyl, amino or amido; and
R$^5$ and R$^6$ taken together with the nitrogen atom to which each is attached form an aromatic or non-aromatic ring, having at least one nitrogen atom, selected from the group consisting of morpholinyl, piperidinyl, pyridyl, pyridinyl, pyrrolyl, pyrrolidinyl, pyrrolidinonyl, and quinuclidinyl.

2. A compound of the formula:

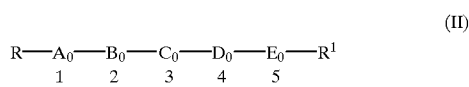

or a pharmaceutically acceptable salt, ester, or prodrug thereof, wherein:

A$_0$ is selected from
3-(1-naphthyl)-D-alanyl,
D-tryptyl,
D-3-(4,4'-biphenyl)alanyl, and
D-(benzthienyl)alanyl;
B$_0$ is seryl;
C$_0$ is an amino acid residue selected from
N-methylphenylalanyl,
(4-N-nitro)-N-methylphenylalanyl,
[4-(3-amino-1,2,4-triazol-5-yl)]phenylalanyl,
[4-(3-amino-1,2,4-triazol-5-yl)]-N-methylphenylalanyl,
(4-N-acetyl)-N-methylphenylalanyl,
(4-N-acetyl)-N-phenylalanyl,
1,2,3,4-tetrahydroisoquinoline-7-hydroxy-3-carbonyl,
1,2,3,4-tetrahydroisoquinoline-3-carbonyl,
sarcosyl,
tyrosyl, and
N-methyltyrosyl;
or where B$_0$ and C$_0$ taken together form an amino acid derivative having the formula:

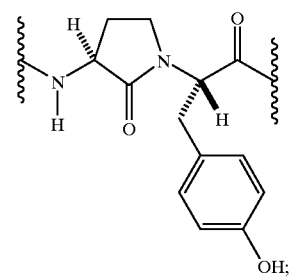

D$_0$ is an amino acid residue selected from
glycyl,
D-diethyl-homoarginyl,
D-(N-epsilon-nicotinyl)lysyl,
N-methylphenylalanyl,
phenylalanyl,
D-phenylalanyl,
D-[4-(3-amino-1,2,4-triazol-5-yl)]-phenylalanyl, and
D-(4-N-acetyl)-phenylalanyl; and
E$_0$ is an amino acid residue selected from
glycyl,
leucyl, and
N-methylleucyl;
or where D$_0$ and E$_0$ taken together form an amino acid derivative having the formula:

23

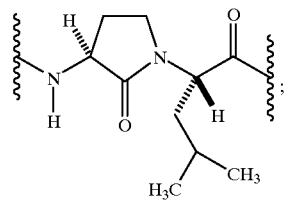

wherein R and $R^1$ are as previously defined.

3. A compound according to claim 1, wherein X is hydrogen or halide; Y is hydrogen; and n is 1–3.

4. A compound according to claim 3, wherein R is 4-fluorophenylpropionyl.

5. A compound according to claim 1, wherein $R^1$ is of the formula —NH—$(CH_2)_n$—$NR^5R^6$ and $R^5$ and $R^6$ taken together with the nitrogen atom to which each is attached form an aromatic or non-aromatic ring, having at least one nitrogen atom, selected from the group consisting of morpholinyl, piperidinyl, pyridyl, pyridinyl, pyrrolyl, pyrrolidinyl, pyrrolidinonyl, and quinuclidinyl.

6. A compound according to claim 5, wherein $R^1$ is —NH—$CH_2$—$CH_2$-(1-pyrrolidine).

7. A compound, or a pharmaceutically acceptable salt, ester, or prodrug thereof, selected from:

4-F-Phenylpropionyl-D1Nal-Ser-NMeTyr-DLys(Nic)-Leu-NH—$(CH_2)_2$-(1-pyrrolidine);

4-F-Phenylpropionyl-D1Nal-Ser-NMeTyr-Gly-Leu-NH—$(CH_2)_2$-(1-pyrrolidine);

4-F-Phenylpropionyl-D1Nal-Ser-Sar-DLys(Nic)-Leu-NH—$(CH_2)_2$-(1-pyrrolidine);

4-F-Phenylpropionyl-D1Nal-Ser-Sar-DLys(Nic)-Gly-NH—$(CH_2)$2-(1-pyrrolidine);

4-F-Phenylpropionyl-Gly-Ser-Sar-DLys(Nic)-Leu-NH—$(CH_2)_2$-(1-pyrrolidine);

4-F-Phenylpropionyl-D1Nal-Gly-NMeTyr-DLys(Nic)-Leu-NH—$(CH_2)_2$-(1-pyrrolidine);

4-F-Phenylpropionyl-D1Nal-Ser-Tyr-DLys(Nic)-Leu-NH—$(CH_2)_2$-(1-pyrrolidine);

4-F-Phenylpropionyl-D1Nal-Ser-NMeTyr-Gly-NMeLeu-NH—$(CH_2)_2$-(1-pyrrolidine);

4-F-Phenylpropionyl-D1Nal-Gly-NMeTyr-Gly-NMeLeu-NH—$(CH_2)_2$-(1-pyrrolidine);

4-F-Phenylpropionyl-DTrp-Ser-NMeTyr-DLys(Nic)-Leu-NH—$(CH_2)_2$-(1-pyrrolidine);

4-F-Phenylpropionyl-DBiphe-Ser-NMeTyr-DLys(Nic)-Leu-NH—$(CH_2)_2$-(1-pyrrolidine);

4-F-Phenylpropionyl-DBiphe-Ser-NMePhe-DLys(Nic)-Leu-NH—$(CH_2)_2$-(1-pyrrolidine);

4-F-Phenylpropionyl-DBiphe-Ser-OHTic-DLys(Nic)-Leu-NH—$(CH_2)$2-(1-pyrrolidine);

24

4-F-Phenylpropionyl-1Nal-Ser-NMeTyr-DLys(Nic)-Leu-NH—$(CH_2)_2$-(1-pyrrolidine);

4-F-Phenylpropionyl-DTrp-Ser-NMeTyr-DPhe-Leu-NH—$(CH_2)$2-(1-pyrrolidine);

4-F-Phenylpropionyl-D1Nal-Pro-NMeTyr-DLys(Nic)-Leu-NH—$(CH_2)_2$-(1-pyrrolidine);

4-F-Phenylpropionyl-D1Nal-Ser-Tic-DLys(Nic)-Leu-NH—$(CH_2)_2$-(1-pyrrolidine);

4-F-Phenylpropionyl-D1Nal-Ser-NMeTyr-6,7[2-(S-3-amino-2-oxo-pyrrolidin-1-yl)-S-2-isopropylmethylacetyl]-NH—$(CH_2)_2$-(1-pyrrolidine);

4-F-Phenylpropionyl-D1Nal-6,7[2-(S-3-amino-2-oxo-pyrrolidin-1-yl)-S-2-(para-hydroxyl)phenylacetyl]-DLys(Nic)-Leu-NH—$(CH_2)_2$-(1-pyrrolidine);

4-F-Phenylpropionyl-D1Nal-Ser-Lys(Nic)-DLys(Nic)-Leu-NH—$(CH_2)$2-(1-pyrrolidine);

4-F-Phenylpropionyl-D1Nal-Ser-NMeTyr-DCit-Leu-NH—$(CH_2)_2$-(1-pyrrolidine);

4-F-Phenylpropionyl-D1Nal-Ser-Arg-DTrp-Leu-NH—$(CH_2)_2$-(1-pyrrolidine);

4-F-Phenylpropionyl-D1Nal-Ser-NMeTyr-DArg-Leu-NH—$(CH_2)_2$-(1-pyrrolidine);

4-F-Phenylpropionyl-D1Nal-Ser-NMePhe(4-$NO_2$)-DCit-Leu-NH—$(CH_2)_2$-(1-pyrrolidine);

4-F-Phenylpropionyl-D1Nal-Ser-NMePhe(4-NAc)-DPhe(NAc)-Leu-NH—$(CH_2)_2$-(1-pyrrolidine);

4-F-Phenylpropionyl-D1Nal-Ser-NMePhe(4-Atza)DPhe(4-Atza)-Leu-NH—$(CH_2)_2$-(1-pyrrolidine);

4-F-Phenylpropionyl-D1Nal-Ser-Phe(4-Atza)DPhe(4-Atza)-Leu-NH—$(CH_2)$2-(1-pyrrolidine);

4-F-Phenylpropionyl-D1Nal-Ser-NMeTyr-DLys(Nic)-Leu-N'-isp-aminoethyl amide;

4-F-Phenylpropionyl-D1Nal-Ser-NMeTyr-DLys(Nic)-Leu-guanidinobutyl amide;

4-F-Phenylpropionyl-D1Nal-Ser-NMeTyr-DLys(Nic)-Leu-N'-isp-aminopenthyl amide;

4-F-Phenylpropionyl-D1Nal-Ser-NMeTyr-DLys(Nic)-Leu-(3-quinuctidinyl)-amide;

4-F-Phenylpropionyl-D1Nal-Ser-NMeTyr-DLys(Nic)-Leu-aminoethyl amide;

4-F-Phenylpropionyl-D1Nal-Ser-NMeTyr-DLys(Nic)-Leu-aminobutyl amide; and

4-F-Phenylpropionyl-D1Nal-Ser-NMeTyr-DLys(Nic)-Leu-aminopentyl amide.

8. A formulation comprising a compound of formula (I) in claim 1 and a pharmaceutically acceptable salt, ester, or prodrug thereof.

* * * * *

UNITED STATES PATENT AND TRADEMARK OFFICE
CERTIFICATE OF CORRECTION

PATENT NO.    : 6,297,354 B1
DATED         : October 2, 2001
INVENTOR(S)   : F. Haviv It is certified that error appears in the above-identified patent and that said Letters Patent is hereby corrected as shown below:

Title page,
Item [54], Title, replace "PENTAPEPTIDE LHRH ANTAGONIST" with
-- PENTAPEPTIDE LHRH ANALOGS --.

Column 21,
Line 61, replace "1 is 0-10, m is 1-2, n is 1-10, p is 1-10;" with -- $L$ is 0-10, $m$ is 1-2, $n$ is 1-10, $p$ is 1-10 --.

Column 23,
Line 35, replace "-(CH$_2$)2-" with -- -(CH$_2$)$_2$- --.
Line 55, replace "(CH$_2$)2-" with -- -(CH$_2$)$_2$- --.

Column 24,
Line 4, replace "-(CH$_2$)2-" with -- -(CH$_2$)$_2$- --.
Line 17, replace "- (CH$_2$)2" with -- -(CH$_2$)$_2$- --.
Line 33, replace "–(CH$_2$)$_2$-" with -- -(CH$_2$)$_2$- --.
Line 43, replace "-(3-quinuctidinyl)-" with -- – (3-quinuclidinyl)- --.

Signed and Sealed this

Third Day of September, 2002

Attest:

Attesting Officer

JAMES E. ROGAN
Director of the United States Patent and Trademark Office